(12) United States Patent
Giordano et al.

(10) Patent No.: US 11,246,634 B2
(45) Date of Patent: Feb. 15, 2022

(54) END CAP FOR INTRAMEDULLARY NAIL (71) Applicant: OrthoPediatrics Corp., Warsaw, IN (US)

(72) Inventors: Michael Giordano, Osceola, IN (US); Chris M. Powers, Warsaw, IN (US)

(73) Assignee: OrthoPediatrics Corp., Warsaw, IN (US)

( * ) Notice: Subject to any disclaimer, the term of this patent is extended or adjusted under 35 U.S.C. 154(b) by 0 days.

(21) Appl. No.: 15/969,215

(22) Filed: May 2, 2018

(65) Prior Publication Data
US 2018/0317982 A1 Nov. 8, 2018

Related U.S. Application Data (60) Provisional application No. 62/500,229, filed on May 2, 2017.

(51) Int. Cl.
*A61B 17/72* (2006.01)
*A61B 17/80* (2006.01)

(52) U.S. Cl.
CPC ...... *A61B 17/7233* (2013.01); *A61B 17/7283* (2013.01); *A61B 17/80* (2013.01)

(58) Field of Classification Search
CPC . A61B 17/72; A61B 17/7291; A61B 17/7241; A61B 17/1725; A61B 17/744; A61B 17/164; A61B 17/864; A61B 17/7233
USPC ...................................... 606/62–68
See application file for complete search history.

(56) References Cited

U.S. PATENT DOCUMENTS

| 4,467,793 | A | * | 8/1984 | Ender ............... A61B 17/7208 606/62 |
| 4,473,069 | A | | 9/1984 | Kolmert |
| 5,443,466 | A | * | 8/1995 | Shah ...................... A61B 17/72 606/323 |
| 5,603,715 | A | * | 2/1997 | Kessler ................. A61B 17/72 606/62 |
| 5,810,817 | A | | 9/1998 | Roussouly et al. |
| 5,976,134 | A | | 11/1999 | Huebner |
| 6,010,506 | A | * | 1/2000 | Gosney ................. A61B 17/72 606/62 |
| 6,030,388 | A | | 2/2000 | Yoshimi et al. |
| 6,077,264 | A | * | 6/2000 | Chemello .......... A61B 17/7225 606/62 |
| 6,299,614 | B1 | | 10/2001 | Kretschmer et al. |
| 7,104,992 | B2 | | 9/2006 | Bailey |
| RE39,325 | E | | 10/2006 | Bryan |
| 7,972,384 | B2 | | 7/2011 | Parsell |
| 9,066,764 | B2 | * | 6/2015 | Perez ................. A61B 17/7233 |
| 9,844,398 | B2 | | 12/2017 | Daniels et al. |
| 10,959,762 | B2 | | 3/2021 | Williams |
| 2004/0138661 | A1 | | 7/2004 | Bailey |
| 2007/0173841 | A1 | * | 7/2007 | Ralph ..................... A61B 17/80 606/86 A |
| 2009/0264933 | A1 | | 10/2009 | Carls et al. |
| 2010/0010490 | A1 | | 1/2010 | Brigido |

(Continued)

FOREIGN PATENT DOCUMENTS

CA 2194966 11/1996

*Primary Examiner* — Eduardo C Robert
*Assistant Examiner* — Tara Rose E Carter
(74) *Attorney, Agent, or Firm* — Gerald W. Roberts; John V. Daniluck; Dentons Bingham Greenebaum LLP (57) ABSTRACT

A means of fastening an intramedullary nail to the surface of a bone.

12 Claims, 5 Drawing Sheets

(56) References Cited

U.S. PATENT DOCUMENTS

| | | |
|---|---|---|
| 2010/0094291 A1 | 4/2010 | DelBello |
| 2011/0184416 A1 | 7/2011 | Rezach et al. |
| 2012/0330313 A1* | 12/2012 | Grady ................ A61B 17/7225 606/64 |
| 2013/0123851 A1 | 5/2013 | Seme et al. |
| 2016/0354127 A1* | 12/2016 | Lundquist ............ A61B 17/809 |

* cited by examiner

END CAP FOR INTRAMEDULLARY NAIL

CROSS REFERENCE TO RELATED APPLICATION

This application claims the benefit of priority to U.S. Provisional Patent Application Ser. No. 62/500,229, filed May 2, 2017, incorporated herein by reference.

FIELD OF THE INVENTION

Various embodiments of the present invention pertain to implants attachable to bones, and in particular to methods and devices for coupling an intramedullary nail to a bone.

BRIEF DESCRIPTION OF THE DRAWINGS

Some of the figures shown herein may include dimensions. Further, some of the figures shown herein may have been created from scaled drawings or from photographs that are scalable. It is understood that such dimensions, or the relative scaling within a figure, are by way of example, and not to be construed as limiting.

ELEMENT NUMBERING

The following is a list of element numbers and at least one noun used to describe that element. It is understood that none of the embodiments disclosed herein are limited to these nouns, and these element numbers can further include other words that would be understood by a person of ordinary skill reading and reviewing this disclosure in its entirety.

| | |
|---|---|
| 10 | bone |
| 12 | intramedullary nail; alternatively implant |
| 14 | assembly tool |
| 20 | end caps |
| 21 | body |
| 22 | angular offset |
| 24 | bone interface surface |
| 30 | bone securement portion |
| 31 | through holes; alt. oval-shaped |
| 32 | axis |
| 33 | depression for fastener head |
| 37 | recess; gap |
| 38 | shoulders squared or angled |
| 40 | nail securement portion |
| 41 | receptacle |
| 42 | aperture; alt. opened end |
| 43 | cylindrical section |
| 44 | reduced diameter section; alt. conical section |
| 45 | exterior |
| 46 | truncated nose |
| 47 | angled sides |
| 48 | axis |

DETAILED DESCRIPTION OF ONE OR MORE EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention, and further permits the reasonable and logical inference of still other embodiments as would be understood by persons of ordinary skill in the art.

It is understood that any reference to "the invention" is a reference to an embodiment of a family of inventions, with no single embodiment including an apparatus, process, or composition that should be included in all embodiments, unless otherwise stated. Further, although there may be discussion with regards to "advantages" provided by some embodiments of the present invention, it is understood that yet other embodiments may not include those same advantages, or may include yet different advantages. Any advantages described herein are not to be construed as limiting to any of the claims. The usage of words indicating preference, such as "preferably," refers to features and aspects that are present in at least one embodiment, but which are optional for some embodiments, it therefore being understood that use of the word "preferably" implies the term "optional."

Although various specific quantities (spatial dimensions, temperatures, pressures, times, force, resistance, current, voltage, concentrations, wavelengths, frequencies, heat transfer coefficients, dimensionless parameters, etc.) may be stated herein, such specific quantities are presented as examples only, and further, unless otherwise explicitly noted, are approximate values, and should be considered as if the word "about" prefaced each quantity. Further, with discussion pertaining to a specific composition of matter, that description is by example only, and does not limit the applicability of other species of that composition, nor does it limit the applicability of other compositions unrelated to the cited composition.

FIGS. 1-8 present various views of a device 20 for securing an implant to a bone. In some embodiments, this apparatus 20 secures an intramedullary nail to the associated long bone. However, the present invention includes yet other uses of the devices shown and claimed, including uses associated with other implants used with a biological unit, and further including non-implant uses.

Figure 1:
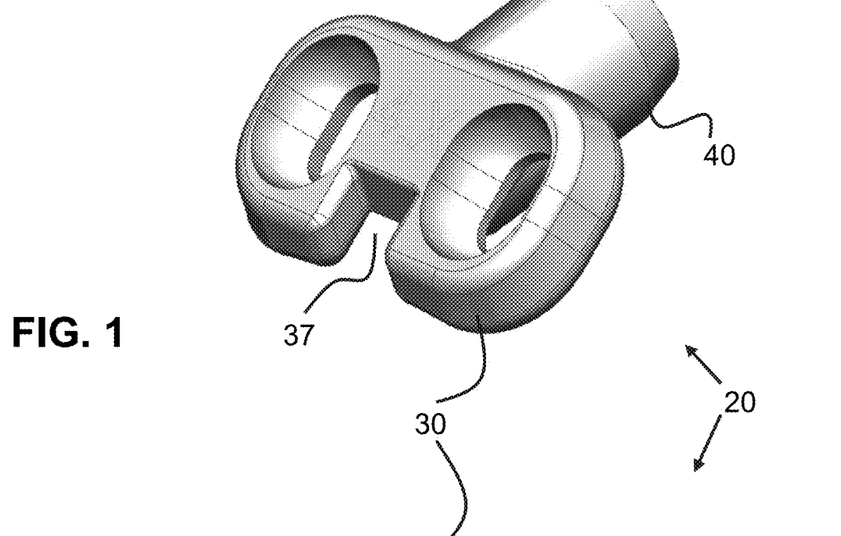
FIG. 1 is a right side perspective view of a bone implant according to one embodiment of the present invention.
Figure 2:
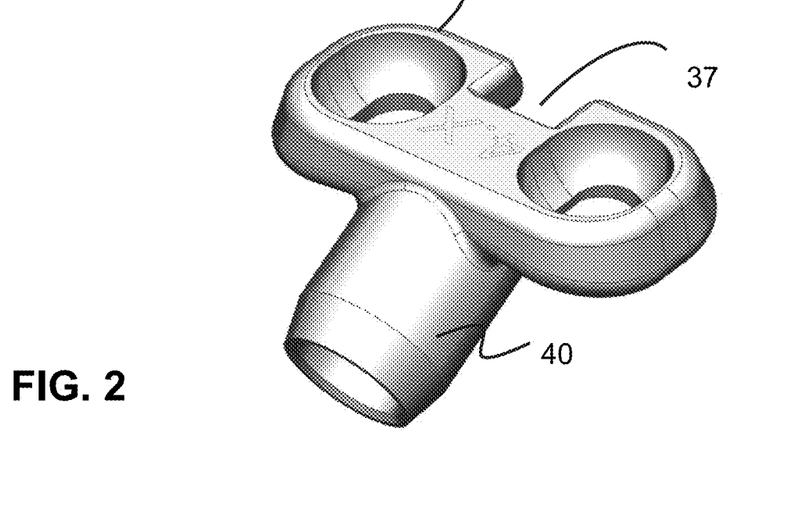
FIG. 2 is a left side perspective of the apparatus of FIG. 1.

In one embodiment, apparatus 20 is an end cap useful for securing the end of an intramedullary nail to a bone. Referring to FIGS. 1 and 2, apparatus 20 comprises a bone securement portion 30 and an implant securement portion 40. Preferably, the two portions are coupled together in a single piece of material, and in those cases in which the devices used with the biological unit, preferably a biocompatible material. Apparatus 20 further includes a recess 37 or gap that, when combined with other features, is useful for accepting a tool by which the user can hold onto and manipulate end cap 20. Such usage will be shown and discussed later with regards to FIGS. 9-12. In addition, yet other embodiments include different types or shapes of the distal ends of portions 30 or 40 for use by gripping or guiding instruments. As examples, feature 37 could also be a protrusion, or could include bayonet-type features for coupling to the instrument.

Figure 3:
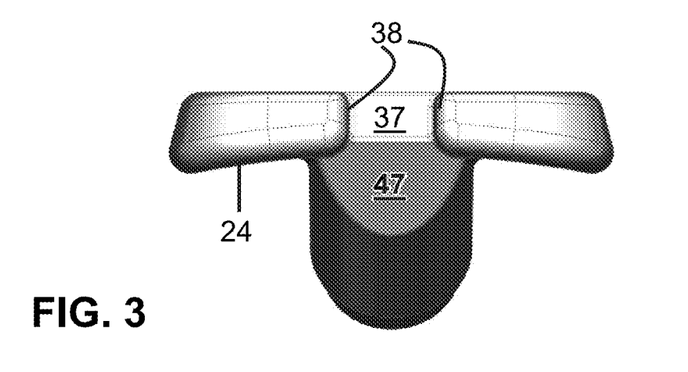
FIG. 3 is an end view of the apparatus of FIG. 1.
Figure 4:
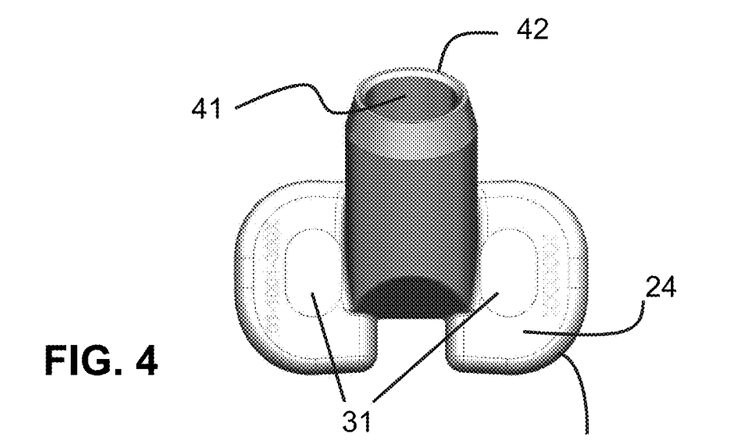
FIG. 4 is a bottom view of the apparatus of FIG. 1.
Figure 5:
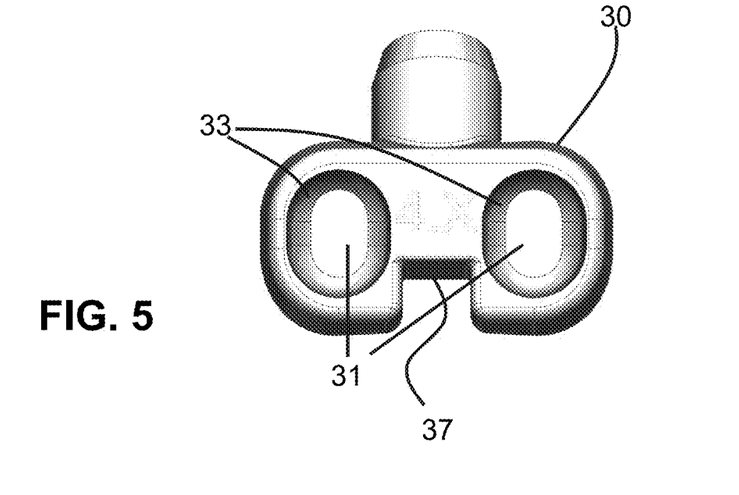
FIG. 5 is a top view of the apparatus of FIG. 1.

FIGS. 3-5 show still further features of device 20. The bone securement portion 30 includes a pair of through holes 31 through each of which a threaded fastener is received for attachment to a platform such as a long bone. In some embodiments, holes 31 are non-circular so as to permit options to the user during attachment of device 20 to the long bone. As shown, holes 31 are oval-shaped. Preferably, each hole 31 is surrounded by a depression that is adapted and configured to receive therein the head of the fastener. The top surface of the received fastener is preferably at about the same height as the top surface shown in FIG. 5 of device 30.

In some embodiments, the holes 31 are defined by axes that are generally parallel to each other. However, yet other embodiments of the present invention contemplate attachment holes in which the received fasteners are oriented with non-parallel axes. In one such example, the axes of the received fasteners converge toward each other at a location within the bone. In still other embodiments, the axes are substantially perpendicular to the curvature of the bone (or alternatively, to the underside curvature 24). Further, although what has been shown and described are a pair of fastening holes located on either side of implant securement portion 40, yet other embodiments of the present invention contemplate different geometric arrangements. As one example, in some embodiments there is only a single fastening hole. In still further embodiments, there can be more than two fastening holes, such as a 2×2 arrangement of fastening holes in a square or V shape.

FIG. 3 depicts a curved interface 24 that extends across the underside of the bone securement portion 30. Preferably, the shape of the underside surface 24 is similar to the shape of the portion of the bone to which device 20 will be attached. As shown in FIG. 3, the underside 24 has a generally constant radius, which is about the same as the exterior radius of the bone in the region where the attachment will be made. However, yet other embodiments of the present invention are not so constrained, and include underside surfaces 24 of any shape that permits a generally uniform contact and bearing surface against the bone. As one example, underside 24 could be a complex curvature. As another example, underside 24 can also be a substantially flat surface.

Figure 6:
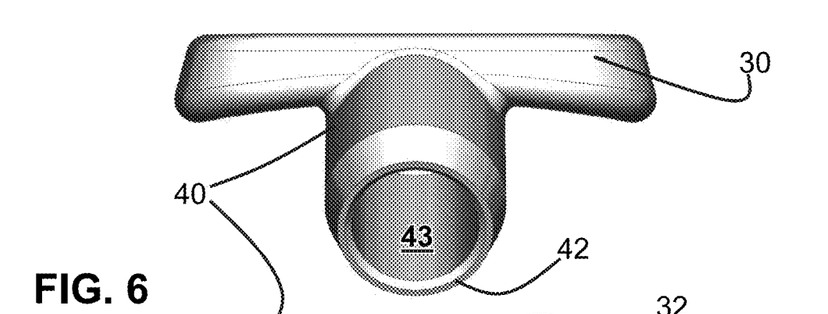
FIG. 6 is an end view of the apparatus of FIG. 1.
Figure 7:
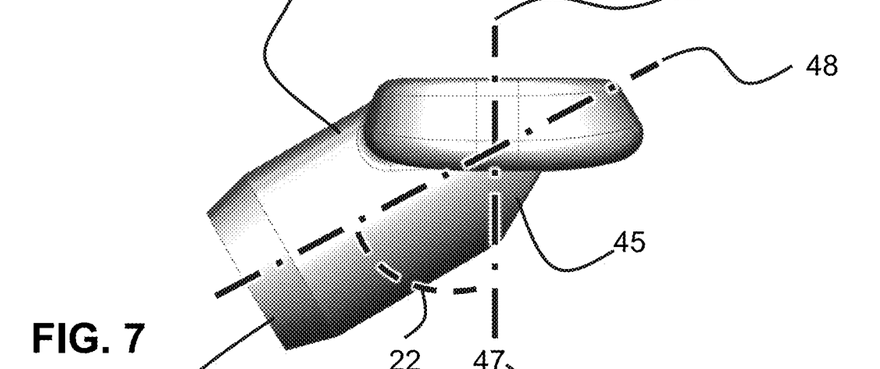
FIG. 7 is a side view of the apparatus of FIG. 1.
Figure 8:
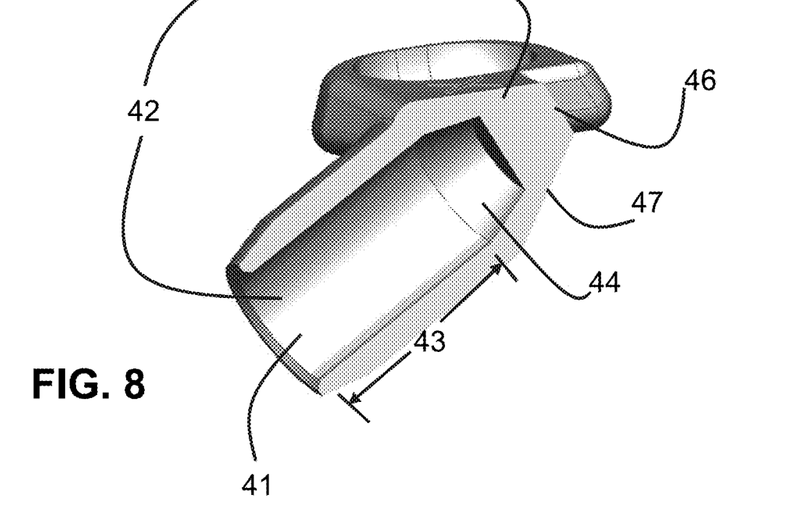
FIG. 8 is a perspective cutaway view of the apparatus of FIG. 1.

FIGS. 3-8 further depict various views of the nail securement portion 40. Referring to FIG. 6, it can be seen that the nail securement portion 40 defines an aperture 42 of a receptacle 41 that is adapted and configured to receive therein the end of the device being secured by portion 30, which in some embodiments is an intramedullary nail. Referring to FIG. 8, aperture 42 leads to a first section 43 that slidingly receives an intramedullary nail in a generally close fit. Preferably, section 43 is generally cylindrical. However, in those embodiments in which the IM nail has a non-circular cross section, the entrance section 43 preferably has a cross sectional shape that is complementary to the external shape of the nail. As one example, for those nails having a cross or "T" shape, the entrance portion 43 of receptacle 41 is likewise cross-shaped or T-shaped. However, yet other embodiments contemplate an internal shape for support receptacle 41 that differs from the cross sectional shape of the IM nail, such as a T-shaped nail being received within a generally cylindrical entrance section.

FIG. 8 shows that receptacle 41 in some embodiments is a closed receptacle, and opened only with regards to aperture 42. FIG. 8 shows the internal closed end 44. This closed end 44 is adapted and configured to provide a tight fit and general securement of the nail to the securement portion 40. As shown in FIG. 8, section 44 is generally conical in shape, with the smallest diameter of the conical shape being smaller than the outer diameter of the nail. However, in yet other embodiments the reduced diameter section 44 can be of any shape. Preferably, the end of the intramedullary nail forms an interference fit with reduced diameter section 44.

Although receptacle 41 has been shown and described with a closed end, various embodiments of the present invention are not so constrained. In some embodiments receptacle 41 is open at each end, such that the end of the nail can be seen when end cap 20 is installed. Further, although an interference fit has been shown and described, the present invention contemplates any manner of coupling the IM nail to securement portion 40. In some embodiments, the sidewall of securement portion 40 is adapted and configured to receive one or more set screws that can be tightened by the medical professional to enhance the frictional fit between the outer surface of the IM nail and the securement portion 40. In still other embodiments the end of the IM nail received within receptacle 41 is adapted and configured to receive a threaded fastener, with this threaded fastener being attached to the IM nail through the second opened end of the receptacle after the end of the nail has been placed in the receptacle. Still further embodiments contemplate the use of a biocompatible adhesive within a receptacle 41 (whether completely opened or closed on one end) to adhesively couple the nail to the securement portion 40.

Referring to FIGS. 7 and 8, it can be seen that the securement portions 30 and 40 establish an angular relationship that permits mounting of device 20 to the side surface of a bone while receiving a nail extending out of the bone from the interior of the bone. FIG. 7 shows this angular relationship between the axes 48 of receptacle 41 and the axes 32 of a hole 31. Preferably, angle 22 is an oblique angle, such that axes 32 and 48 are neither parallel to each other nor perpendicular to each other. However, yet other embodiments contemplate still further angular relationships. As one example, the two axes could be parallel for those implant arrangements in which the geometry of the bone and nail permit parallel orientation. As another example, the two axes could be generally perpendicular when the selected mounting surface of the bone permits perpendicular orientation.

Referring to FIG. 7, it can be seen that the axes 32 and 48 intersect proximate to the location of the fastener where the fastener shank meets the fastener head. Recognizing that some of the IM nail loads are applied along axis 48, such a location on the fastener for these loads to be applied results in good management of the moment applied to the fastener head. However, in some embodiments it is acceptable to have a different location for the intersection of axes 32 and 48. As one example, in some embodiments the intersection is moved downward (referring to FIG. 7), such that portion 40 is shifted downward relative to portion 30. Although this location may increase the moment applied to the fastener head, the downward shift of portion 40 allows for different angular relationships between axes 32 ad 48, such as a generally perpendicular relationship.

FIGS. 3 and 8 further depict external features of device 20 that are adapted and configured for coupling to an insertion instrument. In some embodiments, the closed end of receptacle 41 comprises a pair of angled surfaces 47 that converge toward each other at a truncated nose 46. An insertion tool 14 (shown in FIG. 10) has an end shape that is generally complementary to angled sides 47 and nose 46. The medical professional is able to securely and temporarily use instrument 14 to manipulate device 20 onto the end of the nail 12, and further to hold device 20 in place as the holes in the bone are established and as the fasteners couple device 20 to the bone.

Figure 9:
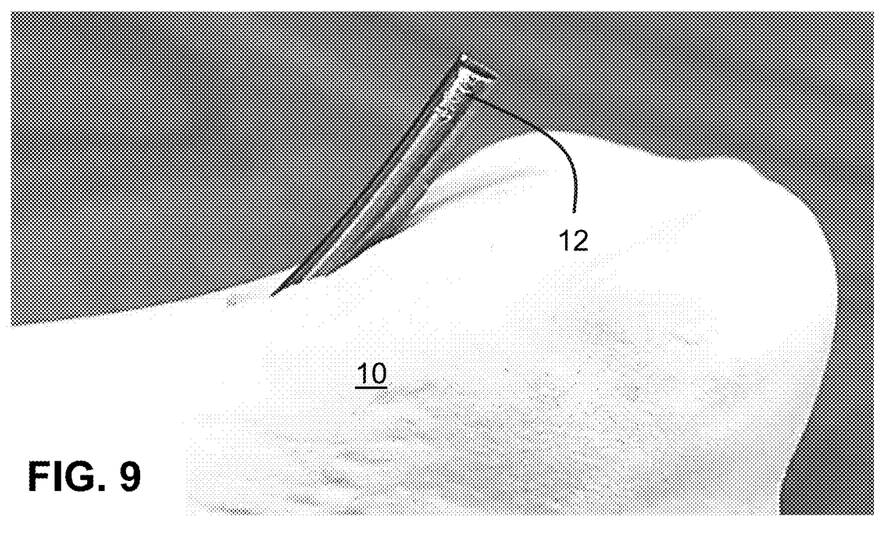
FIG. 9 shows a long bone with an intramedullary nail extending out of the bone.
Figure 10:
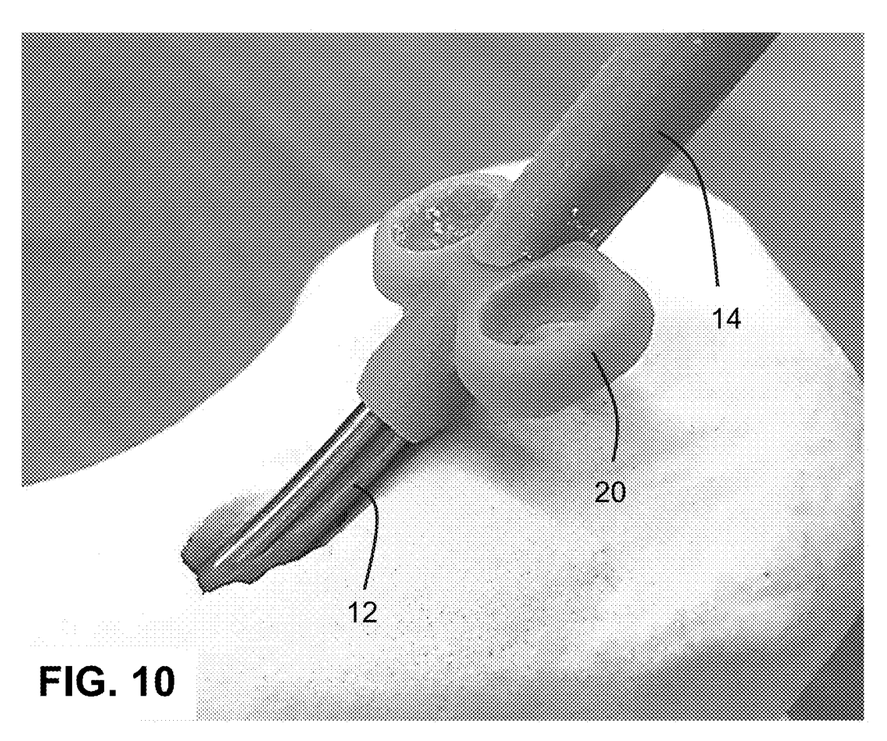
FIG. 10 shows the apparatus of FIG. 1 being coupled to the end of the intramedullary nail by an instrument.
Figure 11:
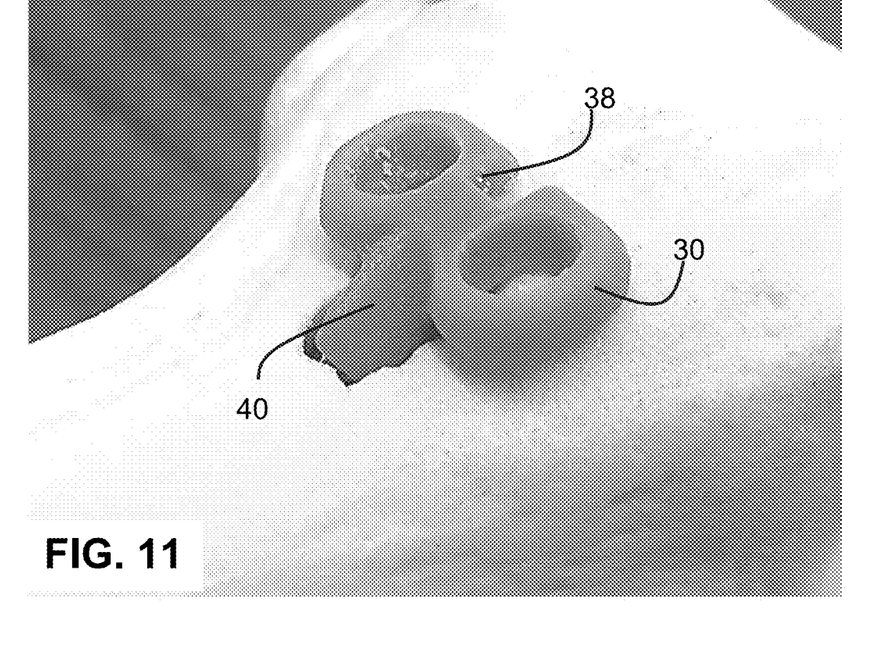
FIG. 11 shows the apparatus of FIG. 1 fully inserted onto the intramedullary nail and in contact with an external surface of the bone.
Figure 12:
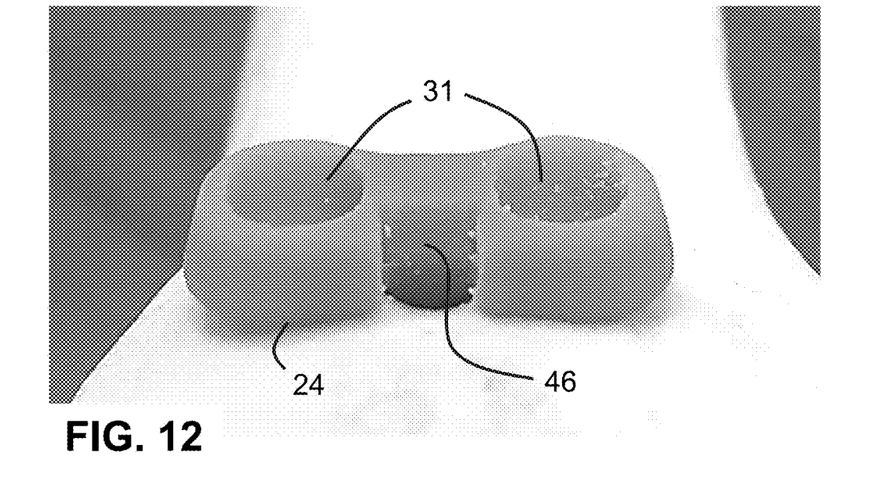
FIG. 12 is an end view of FIG. 11.

FIGS. 9-12 depict the attachment of an end cap 20 to a nail 12 in a long bone. FIG. 9 shows the end of IM nail 12 curving outward from the interior of a long bone 10. FIG. 10 shows an assembly tool 14 being used to position an end cap 20 onto the free end of the IM nail. FIGS. 11 and 12 show the end cap installed on the nail and in contact with the surface of the bone. As best seen in FIG. 12, the curved under surface is in close proximity to the curved outer surface of the long bone 10.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. An implant for use with a bone fastener to couple an intramedullary nail inserted into an interior of a bone to an exterior surface of the bone, the implant comprising:
    a body having a bone securement portion and a nail securement portion;
    wherein said bone securement portion includes a first surface arranged to bear on the exterior surface of the bone; wherein said bone securement portion defines at least one through hole extending through said first surface; wherein said through hole is adapted and configured to receive the bone fastener therethrough; wherein said through hole has a first axis;
    wherein said nail securement portion defines a receptacle having an opened first end, a second end opposing said first end, and a first section extending between said opened first end and said second end; wherein said opened first end, said second end, and said first section are aligned along a second axis; wherein said opened first end and said first section are adapted and configured to slidingly receive therein a first portion of the intramedullary nail; wherein said second end is adapted and configured to secure at least some portion of the first portion of the intramedullary nail to the nail securement portion;
    wherein said receptacle excludes a channel adapted and configured for passage of the intramedullary nail into the interior of the bone through said channel;
    wherein said first axis and said second axis are not parallel; and wherein said first axis and said second axis are arranged such that said opened first end of said receptacle is oriented toward the interior of the bone when said bone securement portion is fastened on the exterior surface of the bone.

2. The implant of claim 1, wherein said first surface is adapted and configured to engage a curving exterior surface of the bone, and said first surface is curved complementary to the curving surface of the bone.

3. The implant of claim 2, wherein said first surface is generally cylindrical.

4. The implant of claim 1, wherein the at least some portion of the first portion of the intramedullary nail is an end portion of the intramedullary nail.

5. The implant of claim 1, wherein at least one of said first section of said receptacle and said second end of said receptacle is adapted and configured to frictionally couple to the first portion of the intramedullary nail.

6. The implant of claim 1, wherein said nail securement portion has a first shape that is adapted and configured for coupling to a holding tool having a second shape that is complementary to the first shape.

7. The implant of claim 1, wherein said first surface of said bone securement portion is flat.

8. The implant of claim 1, wherein said first axis is oblique to said second axis.

9. The implant of claim 1, wherein said first axis is perpendicular to second axis.

10. The implant of any one of claim 1-4, 5, 6-8 or 9, wherein said first section is cylindrical and has a first inner diameter, said second end is generally conical and includes an end portion having a second inner diameter, and said second inner diameter is smaller than said first inner diameter.

11. An implant for coupling an exterior surface of a bone to an intramedullary nail, comprising:
    a body having an integral bone securement portion and an integral nail securement portion;
    said bone securement portion including at least one through hole adapted and configured to receive therein a bone fastener, the through hole having a first axis; and
    said nail securement portion defining a receptacle having an opened end and a closed end both aligned along a second axis, the receptacle being adapted and configured for receiving therein a portion of an intramedullary nail, wherein an interior surface of the receptacle proximate to the closed end includes a conical portion;
    wherein the first axis and the second axis are adapted and configured such that the opened end of the receptacle is oriented toward the interior of a long bone when the bone securement portion is fastened on the exterior surface of the long bone;
    wherein the angle between the first axis and the second axis is perpendicular.

12. An implant for coupling an exterior surface of a bone to an intramedullary nail, comprising:
    a body having an integral bone securement portion and an integral nail securement portion;
    said bone securement portion including a first through hole adapted and configured to receive therein a bone fastener and a second through hole adapted and configured to receive therein a bone fastener, the first through hole having a first axis; and
    said nail securement portion defining a receptacle having an opened end and a closed end both aligned along a second axis, the receptacle being adapted and configured for receiving therein a portion of an intramedullary nail;
    wherein the first axis and the second axis are adapted and configured such that the opened end of the receptacle is oriented toward the interior of a long bone when the bone securement portion is fastened on the exterior surface of the long bone, wherein the first hole and the second hole are located on opposite sides of the second axis;

wherein an angle between the first axis and the second axis is perpendicular.

* * * * *